United States Patent [19]
Neely

[11] Patent Number: 5,504,090
[45] Date of Patent: Apr. 2, 1996

[54] COMPOSITIONS AND METHODS FOR THE PREVENTION AND TREATMENT OF ISCHEMIA-REPERFUSION ORGAN INJURY

[75] Inventor: Constance F. Neely, Philadelphia, Pa.

[73] Assignee: Trustees of the University of Pennsylvania, Philadelphia, Pa.

[21] Appl. No.: 219,946

[22] Filed: Mar. 30, 1994

[51] Int. Cl.$^6$ ............................ A61K 31/52; C07D 473/04
[52] U.S. Cl. ........................... 514/263; 514/266; 514/262; 514/261; 544/267
[58] Field of Search ................................. 514/266, 263, 514/262, 261; 544/264, 265, 266, 267

[56] References Cited

U.S. PATENT DOCUMENTS

| | | | |
|---|---|---|---|
| 4,548,818 | 10/1985 | Kjellen et al. | 514/263 |
| 4,593,095 | 6/1986 | Synder et al. | 544/272 |
| 4,769,377 | 9/1988 | Synder et al. | 514/263 |
| 4,772,607 | 9/1988 | Badger et al. | 514/263 |
| 4,783,530 | 11/1988 | Rzeszotarski et al. | 544/267 |
| 4,968,672 | 11/1990 | Jacobson et al. | 514/46 |
| 5,032,593 | 7/1991 | Rzeszotarski et al. | 514/263 |
| 5,068,236 | 11/1991 | Suzuki et al. | 514/263 |
| 5,175,290 | 12/1992 | Rzeszatarski et al. | 544/267 |
| 5,236,908 | 8/1993 | Gruber et al. | 514/46 |
| 5,248,678 | 9/1993 | Costa et al. | 514/220 |
| 5,256,650 | 10/1993 | Peet et al. | 514/46 |
| 5,298,508 | 3/1994 | Jacobson et al. | 514/263 |
| 5,366,977 | 11/1994 | Pollard et al. | 514/263 |

OTHER PUBLICATIONS

Drury AN, Szent-Gyorgi A., "The Physiological Activity of Adenine Compounds[1] with Especial Reference To Their Action Upon The Mammalian Heart", *J. Physiol* (Lond) 68:213–237, 1929.

Burnstock G, "Cholinergic and Purinergic Regulation of Blood Vessels", Handbook of Physiology–The Cardiovascular System II, 2nd Edition, vol. 2, Chapter 19, pp. 567–612, 1979.

Ely, SW et al., "Functional and Metabolic Evidence of Enhanced Myocardial Tolerance to Ischemia and Reperfusion with Adenosine", *J. Thorac Cardiovasc Surg* 90:549–556, 1985.

Olafsson B, et al. "Reduction of Reperfusion Injury in the Canine Preparation by Intracoronary Adenosine: Importance of the Endothelium and the No–Reflow Phenomenon", *Circ* 76:1135–1145, 1987.

Lasley, RD, Mentzer, RM, "Adenosine Improves Recovery of Postischemic Myocardial Function Via an Adenosine $A_1$ Receptor Mechanism", *Am J Physiol* 263:H1460–H1465, 1992.

Ely SW, Berne RM, "Protective Effects of Adenosine in Myocardial Ischemia", *Circ* 85:893–904, 1992.

Janier, MF, et al., "Adenosine Protects Ischemic and Reperfused Myocardium by Receptor–Mediated Mechanisms", *Am J Physiol* 264:H163–H170, 1993.

Zhao, ZQ, et al. "Receptor–Mediated Cardioprotective Effects of Endogenous Adenosine Are Exerted Primarily During Reperfusion After Coronary Occlusion in the Rabbit", *Circ* 88:709–719, 1993.

Brechler V et al., "Activation of $Na^{30}/CA^{2+}$ Exchange by Adenosine in Ewe Heart Sarcolemma Is Mediated by a Pertussis Toxin–Sensitive G Protein", *J Biol Chem* 265:16851–16855, 1990.

Haselton FR et al., "Adenosine Decreases Permeability of In Vitro Endothelial Monolayers", *J Appl Physiol* 74:1581–1590, 1993.

Thornton JD, et al., "Intravenous Pretreatment With $A_1$–Selective Adenosine Analogues Protects the Heart Against Infarction", *Ciur* 85:659–665, 1992 (I).

Lui GS, et al., "Protection Against Infarction Afforded by Preconditioning is Mediated by $A_1$ Adenosine Receptors in Rabbit Heart", *Cir* 84:350–356, 1991.

Thornton JD, "Effect of Adenosine Receptor Blockade: Preventing Protective Preconditioning Depends on Time of Initiation", *Am J Physiol* 265:H504–508, 1993, (II).

Toombs CF, et al., "Myocardial Protective Effects of Adenosine Infract Size Reduction With Pretreatment and Continued Receptor Stimulation During Ischemia", *Circ* 86:986–994, 1992.

Suzuki, F., et al., "Adenosine $A_1$ Antagonists. 2. Structure––Activity Relationships on Diuretic Activities and Protective Effects against Acute Renal Failure", *J. Med Chem*, 35:3066–3075, 1992, (I).

Kellett, R. et al., "Amelioration of Glycerol–Induced Acute Renal Failure in the Rat with 8–cyclopentyl–1, 3–dipropylxanthine", *Br. J. Pharmacol.*, 98:1066–1074, 1989.

Knight, R. J., et al., "Effect of the Selective $A_1$ Adenosine Antagonist 8–cyclopentyl–1, 3–dipropylxanthine on Acute Renal Dysfunction Induced by *Escherichia coli* Endotoxin in Rats", *J. Pharm Pharmacol.*, 45:979–984, 1993.

Neely et al. "Adenosine Does Not Mediate the Pulmonary Vasodilator Response of Adenosine 5'–triphosphate in the Feline Pulmonary Vascular Bed", *J. Pharmacol. and Exp. Therap.*, 250(1):170–176, 1989.

Neely et al., "Adenosine and ATP Produce Vasoconstriction in the Feline Pulmonary Vascular Bed by Different Mechanisms", *J. Pharmacol. and Exp. Therap.*, 258(3):753–761, 1991.

Adkins et al., "Adenosine Prevents PMA–induced Lung Injury Via an A2 Receptor Mechanism", *Appl. Physiol.*, 1993, 74(3):982–988.

Egan TM, et al., *Lung transplantation. Curr Probl Surg* 26:675–751, 1989.

Levinson RM, et al., "Reperfusion Pulmonary Edema After Pulmonary Artery Thromboendarterectomy", *Am Rev Resp Dis* 134:1241–1245, 1986.

Kuratani T, et al., "Experimental Study in a Rabbit Model of Ischemia–reperfusion Lung Injury During Cardiopulmonary Bypass", *J Thorac Cardiovas Surg* 103:564–568, 1992.

(List continued on next page.)

Primary Examiner—Richard L. Raymond
Assistant Examiner—Deborah Lambkin
Attorney, Agent, or Firm—Jane Massey Licata

[57] ABSTRACT

Methods of preventing or inhibiting ischemia-reperfusion injury in an organ by administration of a composition containing a selective $A_1$ adenosine receptor antagonist are provided.

11 Claims, 3 Drawing Sheets

OTHER PUBLICATIONS

Schmeling DJ, et al., "Evidence for Neutrophil–related Acute Lung Injury After Intestinal Ischemia–reperfusion", *Surg* 106:195–201, 1989.

Murata T, et al., "Reperfusion after a Two–Hour Period of Pulmonary Artery Occlusion Causes Pulmonary Necrosis", *Am Rev Resp Dis* 146:1048–1053, 1992.

Hamvas A, et al., "Inflammation and Oxygen Free Radical Formation During Pulmonary Ischemia–reperfusion Injury", *J Appl Physiol* 72:621–628, 1992.

Zamora CA, et al., "Thromboxane Contributes to Pulmonary Hypertension in Ischemia–reperfusion Lung Injury", *J Appl Physiol* 74:224–229, 1993.

Pharmacology and Physiological Roles. Edited by TW Stone, VCH, London, pp. 163–173, 1985.

Cronstein BN, et al., "Adenosine Modulates the Generation of Superoxide Anion by Stimulated Human Neutrophils via Interaction with a Specific Cell Surface Receptor", *Ann NY Acad Sci* 451:291–301, 1985.

COMPOSITIONS AND METHODS FOR THE PREVENTION AND TREATMENT OF ISCHEMIA-REPERFUSION ORGAN INJURY

FIELD OF INVENTION

Ischemia followed by reperfusion in an organ produces structural and functional abnormalities in the tissue of that organ and others. Neutrophil infiltration, hemorrhage, edema and necrosis are all observed in tissues following an ischemia-reperfusion injury. $A_1$ and $A_2$ adenosine receptors play an important role in the mechanisms behind this injury. In the present invention a method is provided which prevents and treats ischemia-reperfusion related organ injury. It has now been found that administration of a composition comprising a selective $A_1$ adenosine receptor antagonist can prevent injuries related to ischemia followed by reperfusion in an organ. Compositions of the present invention can be administered prior to harvesting a donor organ which will be transplanted or to a surgical procedure in which ischemia is expected. These compositions can also be used to treat ischemia-reperfusion injury in high risk patients.

BACKGROUND OF INVENTION

Nucleotides and nucleosides and their purinoceptors have been found to be important mediators in determining pulmonary vascular (PV) tone. Nucleotides are autacoids; that is, they are released locally, metabolized locally by stereoselective nucleotidases, and act on their own local receptors to bring about changes in vascular tone, and neutrophil and platelet function. The effects of nucleotides and nucleosides on PV tone were first described in 1929 by Drury and Szent-Gyorgi when they demonstrated that the nucleoside adenosine produced a fall in arterial pressure and a rise in pulmonary artery pressure in dogs and cats. Drury AN, Szent-Gyorgi A, J. Physiol (Lond) 68:213–237, 1929. Since this discovery, much research has been performed to characterize the role of adenosine and its specific purinoceptors.

Based on pharmacological analysis in isolated systemic vessels, Burnstock originated the purinergic receptor hypothesis. Burnstock G, Handbook of Physiology-The Cardiovascular System II, 2nd Edition, Volume 2, Chapter 19, pp 567–612, 1979. Adenosine-sensitive receptors, referred to as $P_1$ receptors, were characterized as having an agonist potency in the order of adenosine>AMP>ADP>ATP. These receptors were found to act via an adenylate cyclase system and were antagonized by methylxanthines. Since the original classification was made $P_1$ receptors have been subdivided into $A_1$ and $A_2$ receptors based upon their effect on adenylate cyclase, receptor affinity and radioligand binding.

$A_1$ receptors inhibit adenylate cyclase activity. High affinity $A_1$ receptors have been identified in brain, heart, lung, kidney, skin, pancreas, stomach, spinal cord, intestines, vas deferens, liver, spleen, testis, adrenergic nerve terminals, white blood cells and fat cells. These receptors preferentially bind the purine moiety of adenosine and the order of potency of adenosine analogues is R-phenylisopropyladenosine (R-PIA)>cyclohexyladenosine (CHA)>5'-N-ethylcarboxamidoadenosine (NECA)=2-chloroadenosine (2-CA) >S-phenylisopropyladenosine (S-PIA).

$A_2$ receptors, on the other hand, stimulate adenylate cyclase activity. Low affinity $A_2$ receptors have been identified in brain, heart, lung, thymus, spleen, epididymis, vas deferens, adipose tissue, vascular smooth muscle cells, platelets, fibroblasts, lymphocytes, neutrophils and pheochromocytoma cells. They preferentially bind the ribose moiety of adenosine and follow a potency order NECA>2-CA>R-PIA=CHA>S-PIA. $A_2$ receptors have been identified in coronary arteries and 2-phenylaminoadenosine (CV1808) was second only to NECA as the most potent coronary vasodilator.

In the heart, $A_1$ adenosine receptors mediate negative inotropic and negative chronotropic effects while $A_2$ receptors mediate coronary vasodilation. Effects of agonists and antagonists on $A_1$ and $A_2$ adenosine receptors have been reported.

Adenosine has been reported to attenuate ischemiareperfusion injury of the heart upon administration prior to ischemia or reperfusion. Ely, SW et al., J. Thorac Cardiovasc Surg 90:549–556, 1985; Olafsson B, et al. Circ 76:1135–1145, 1987; Lasley, RD, et al., Am J Physiol 263:H1460–H1465, 1992; Ely SW, Berne RM, Circ 85:893–904, 1992; Janier, MF, et al., Am J Physiol 264:H163–H170, 1993; Zhao, ZQ, et al. Circ 88:709–719, 1993. Following 90 minutes of ischemia, an intracoronary infusion of adenosine during reperfusion reduced infarct size, improved regional myocardial blood flow and ventricular function, decreased neutrophil infiltration of the ischemic zone of the myocardium and leukocyte plugging of capillaries, and was associated with preservation of endothelial cell structure. Olafsson B et al., Circ 76:1135–1145, 1987. The mechanisms by which adenosine attenuates the injury in the heart following ischemia and reperfusion are not completely understood. However, it has been determined that by acting on $A_1$ adenosine receptors, adenosine inhibits the release of neurotransmitter substances, produces negative inotropic and chronotropic responses in the heart, attenuates Ca2+ overload of cells, and increases glycolytic flux. Ely SW, Berne RM, Circ 85:893–904, 1992; Brechler V et al., J Biol Chem 265:16851–16855, 1990. By acting on $A_2$ adenosine receptors, adenosine produces vasodilation, inhibits oxygen radical release from neutrophils, neutrophil migration, and adherence of activated neutrophils to endothelial cells, inhibits platelet aggregation, and decreases edema formation. Ely SW, Berne RM, Circ 85:893–904; Haselton FR et al., J Appl Physiol 74:1581–1590, 1993. Adenosine also serves as the primary substrate for ATP synthesis by the purine salvage pathway. When administered prior to ischemia, selective $A_1$ adenosine receptor agonist, R-PIA, has also been reported to attenuate ischemia-reperfusion injury in the heart. Thornton JD, et al., Cir 85:659–665, 1992. In addition, brief episodes of ischemia (approximately 5 to 15 minutes), also referred to as preconditioning ischemia, have been reported to attenuate ischemia-reperfusion injury in the heart. Thornton JD, et al., Cir 85:659–665, 1992; Lui GS, et al., Circ 84:350–356, 1991; Thornton JD, Am J Physiol 265:H504–508, 1993. However, the positive effects of adenosine and preconditioning ischemia were found to be antagonized by a selective $A_1$ receptor antagonist 8-cyclopentyl-1, 3-dipropylxanthine (DPCPX) and a nonselective adenosine receptor antagonist 8-(p-sulfophenyl) theophylline (8-SPT), respectively. Lasley, RD, Mentzer, RM, Am J Physiol 263:H1460–H1465, 1992; Thornton JD, Am J Physiol 265:H504–508, 1993; Toombs CF, et al., Circ 86:986–994, 1992.

In contrast to the heart, adenosine has been reported to cause vasoconstriction in the kidney. $A_1$ receptor stimulation in the kidney was shown to produce primary vasoconstriction of the afferent arteriole and a decrease in glomerular filtration rate. Suzuki, F., et al., J. Med Chem, 35:3066–3075, 1992. Suzuki et al. found selective and potent antagonism of the $A_1$ adenosine receptor to be important in diuretic and natriuretic activities of the kidney.

It has also been suggested that selective $A_1$ adenosine receptor blockade is more effective in ameliorating acute renal failure than non-selective antagonism of both the $A_1$ and $A_2$ receptors. Kellett, R. et al., *Br. J. Pharmacol.*, 98:1066–1074, 1989. However, Knight, R. J., et al., *J. Pharm Pharmacol.*, 45:979–984, 1993, showed that a selective $A_1$ adenosine antagonist could only provide protection against endotoxin-induced renal dysfunction in the rat in animals receiving a high dose of endotoxin. Coadministration of the $A_1$ selective adenosine antagonist DPCPX resulted in statistically significant attenuation of the reduction of renal blood flow and inulin clearance in animals receiving a high dose but not a low dose of endotoxin. From these results Knight et al. concluded that adenosine does not play a major role in the pathophysiology of endotoxemic ARF.

Adenosine has also been reported to act upon adenosine $P_1$ receptors in the pulmonary vascular bed to induce vasoconstriction and vasodilation. Neely et al. *J. Pharmacol. and Exp. Therap.*, 250(1):170–176, 1989. Further investigations were undertaken to understand the mechanisms mediating vasoconstrictor responses to adenosine in the lung in the intact-chest, spontaneously breathing cat under conditions of controlled blood flow and constant left atrial pressure. It was found that adenosine induces vasoconstriction in the lung by acting on an adenosine $A_1$ -"like" receptor. An $A_1$ selective agonist was approximately 10 to 30 times more potent than adenosine. It was also found that vasoconstriction response was dependent on formation of thromboxane A2. Neely et al., *J. Pharmacol. and Exp. Therap.*, 258(3):753–761, 1991. It has also been reported that phorbol myristate acetate (PMA) -induced increases in capillary permeability in the isolated blood-perfused dog lung can be blocked by pretreatment with adenosine, which binds the adenosine $A_2$ receptors. When an $A_1$ antagonist, DPCPX, was administered to these animals before PMA introduction in the presence of adenosine, this permeability damage was prevented and the pulmonary vascular resistance remained unchanged from controls. Adkins et al., *Appl. Physiol.*, 1993, 74(3):982–988. Adkins et al. suggest that this finding leads one to postulate that at least portions of the constriction produced with PMA challenge are mediated by activation of Am receptors as evidenced by the blocking effect of DPCPX on the PMA-induced resistance increase. However, as acknowledged by Adkins et al., further studies are required as the mechanisms behind PMA-induced lung injury are poorly understood and exogenous adenosine was present in these experiments. Also, the increase in vascular resistance may not play an important role in lung injury following endotoxin, PMA, or ischemia-reperfusion.

Ischemia-reperfusion injury of the lung occurs after lung transplantation, pulmonary thromboendarterectomy or cardiopulmonary bypass. Egan TM, et al., *Lung transplantation. Curr Probl Surg* 26:675–751, 1989; Levinson RM, et al., *Am Rev Resp Dis* 134:1241–1245, 1986; Kuratani T, et al., *J Thorac Cardiovas Surg* 103:564–568, 1992. Ischemia-reperfusion injury of the lung also occurs after ischemia and reperfusion of distant organs, for example the intestines. Schmeling DJ, et al., *Surg* 106:195–201, 1989. In the lung, two hours of ischemia followed by three hours of reperfusion produced structural and functional abnormalities that did not occur with ischemia alone. Murata T, et al., *Am Rev Resp Dis* 146:1048–1053, 1992; Hamvas A, et al., *J Appl Physiol*72:621–628, 1992. Neutrophil infiltration, hemorrhage and edema formation occurred only following reperfusion. In conscious, intact-chest, spontaneously breathing rats, two hours of ischemia alone was associated with minimal structural changes. Murata T, et al., *Am Rev Resp Dis* 146:1048–1053, 1992. However, two hours of ischemia followed by reperfusion was associated with hemorrhagic necrosis of the lung, disrupted alveoli with exudate, destroyed endothelial cells which were detached from internal elastic lamina, and leukocyte accumulation. In isolated, perfused rabbit lungs, 40 minutes of ischemia (when both ventilation and perfusion were discontinued) followed by 55 minutes of reperfusion was associated with electron microscopic alterations of lung tissue, including gaps between endothelial cell tight junctions, gaps between the capillary lumen and interstitial space and edema formation. Zamora CA, et al., *J Appl Physiol* 74:224–229, 1993. Following ischemia and reperfusion of these rabbit lungs, the rise in pulmonary artery pressure and increase in wet-to-dry lung weight ratios were associated with an increase in thromboxane. These increases were markedly reduced by administration of a thromboxane receptor antagonist, SQ29548, prior to ischemia. Moreover SQ29548 reduced the alterations in endothelial cell gap junctions and interstitial edema formation on electron microscopy.

It has now been found that administration of an effective amount of an $A_1$ adenosine receptor antagonist to organs prior to ischemia prevents ischemia-reperfusion injury in these organs or related tissues. Compositions comprising an $A_1$ adenosine receptor antagonist are useful in the prevention and treatment of ischemia-reperfusion injury following organ transplantation, resulting from surgical procedures, and associated with certain disease states including sepsis.

SUMMARY OF THE INVENTION

An object of the present invention is to provide a method of preventing or inhibiting ischemia-reperfusion organ injury comprising administering to an animal an effective amount of an $A_1$ adenosine receptor antagonist.

Another object of the invention is to provide compositions comprising an $A_1$ adenosine receptor antagonist useful in the prevention or treatment of ischemia-reperfusion organ injury resulting from transplantation, surgical procedures or disease states.

DETAILED DESCRIPTION OF THE INVENTION

Figure 1:
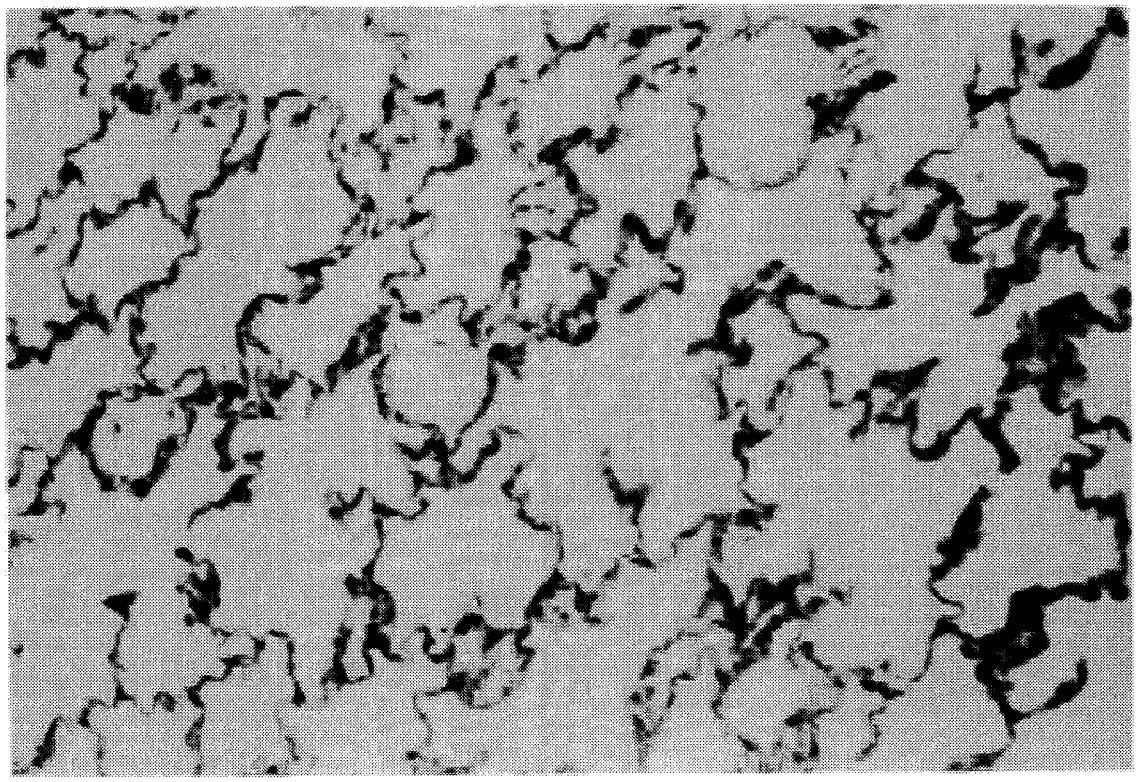
FIG. 1 is a photograph of the alveolar injury in the lung of cat resulting from two hours of ischemia followed by reperfusion wherein the cat was pretreated with the Am adenosine receptor antagonist, XAC (0.075 mg/kg/hour), administered as a intralobar infusion for 30 minutes prior to ischemia.

ATP, which is released during ischemia, is metabolized to adenosine by species-specific ectonucleotidases located on endothelial and vascular smooth muscle cells. ATP and adenosine act on specific extracellular receptors, adenosine-sensitive $P_1$ and ATP-sensitive $P_2$ purinoceptors located on a number of cell types including endothelial and vascular smooth muscle cells, neutrophils, and platelets. These cells are important in the pathophysiology of ischemia-reperfusion injury of organs. A number of complex events occur after ischemia and reperfusion, including the release of cytokines and chemoattractants, activation of neutrophils, adherence of neutrophils to endothelial cells, and the release of oxygen radicals and vasoactive substances, including thromboxane. Following ischemia and reperfusion of the rabbit lung, an increase in thromboxane is associated with an increase in pulmonary vascular tone, alterations in endothelial cell tight junctions and pulmonary edema formation. Zamora CA, et al., *J Appl Physiol* 74:224–229, 1993. Adenosine, via its effects on specific adenosine receptors $A_1$ and $A_2$, effects pulmonary vascular tone, Neely CF, et al., *J. Pharmacol Exp Ther* 250(1):170–176, 1989; platelet function, Hourani SMO, Cusack NJ, *Actions and Structure Activity Relationships of Purines on Platelets.* In Purines. *Pharmacology and Physiological Roles.* Edited by TW Stone, VCH, London, pp 163–173, 1985; and superoxide anion release from neutrophils Cronstein BN, et al., *Ann NY Acad Sci* 451:291–301, 1985. Also, in isolated, blood perfused dog lungs, adenosine was found to attenuate the pulmonary edema following phorbol myristate acetate induced lung injury by acting on $A_2$ adenosine receptors. Adkins et al., *Appl. Physiol.,* 74(3):982–988, 1993.

Adenosine produces vasoconstriction in the feline lung vasculature by acting on $A_1$ adenosine receptors which induce the release of thromboxane. Neely CF, et al., *J Pharmacol Exp Ther* 258:753–761, 1991. By acting on $A_2$ adenosine receptors, adenosine produces vasodilation, inhibition of the migration of neutrophils and adherence of activated neutrophils to endothelial cells, inhibition of oxygen radical release from neutrophils and platelet aggregation, and a decrease in endothelial cell permeability.

Adenosine-sensitive $A_1$ and $A_2$ receptors play important roles in ischemia-reperfusion injury of organs following transplantation, during certain surgical procedures, and following shock or trauma. Adenosine, selective $A_1$ adenosine receptor agonists (when administered prior to ischemia), and brief periods of ischemia (preconditioning ischemia) have been shown to attenuate ischemia-reperfusion injury of the heart.

Such treatments are also believed to attenuate ischemiareperfusion injury of the lung. For example, in lung transplant operations, it is possible for a surgeon to subject a lung to brief periods of ischemia prior to removing the lung from a donor. However, the effects of preconditioning are brief. A more effective treatment would be to administer a drug into the lung which would stay in the lung until transplantation takes place. As $A_1$ adenosine receptors mediate the effects of preconditioning, it has been proposed that administration of a very hydrophobic $A_1$ adenosine receptor agohist such as R-PIA could prove useful in improving the outcome of organ function following transplantation. However, administration of an $A_1$ adenosine receptor agonist can result in several unwanted side effects, including decreased heart rate and myocardial contractility, bronchospasm and a decrease in urine output resulting from decreased kidney function. It has now been found that administering a selective $A_1$ adenosine receptor antagonist attenuates ischemia-reperfusion injury more effectively and without the unwanted side effects.

In the present invention, a method of preventing ischemia-reperfusion organ injury is provided wherein an animal, preferably a human, is administered an effective amount of a selective $A_1$ adenosine receptor antagonist at a selected time prior to a surgical procedure in which ischemia is expected to occur so that the organ injury is prevented. The term "effective amount" refers to a concentration of a selective $A_1$ adenosine receptor antagonist which is sufficient to interfere with the action of adenosine upon this receptor. The term "selected time" refers to an amount of time prior to ischemia which is sufficient to allow a selective adenosine $A_1$ receptor antagonist to bind to the adenosine $A_1$ receptors in the organ prior to ischemia and surgery. If the adenosine $A_1$ receptor antagonist is administered to the organ directly the preferred selected time is from about 20 to 30 minutes, more preferably 30 minutes. If the antagonist is administered intravenously, the selected time may be longer, for example, 30 minutes to an hour. Surgical procedures for which this method is useful include harvesting donor organs for transplantation. Other examples of surgical procedures and organs at risk of ischemia reperfusion injury during these procedures include, but are not limited, brain injury during carotid artery surgery and cerebral vascular surgery; brain, spinal cord, intestine and kidney injury during surgery of the thoracic aorta and kidney injury during abdominal aortic surgery; lung injury following the use of cardiopulmonary bypass during lung and heart surgery; heart injury following revascularization (coronary artery bypass graft surgery); kidney injury following surgery on renal arteries; intestinal injury following surgery on the mesenteric arteries; and skin injury following harvesting of a skin graft.

Methods of the present invention are also useful in treating ischemia-reperfusion organ injury in patients resulting from injuries such as bowel ischemia and reperfusion, sepsis, anaphylaxis, hemorrhagic shock and trauma. For purposes of this application, patients suffering from such injuries are defined as "high risk" patients.

The intact-chest spontaneously breathing cat animal model has been used to create ischemia-reperfusion injury of the lung which is morphometrically similar to this injury in other species and reproducible quantitatively. With the use of fluoroscopy, catheters are placed in the left lower lobe artery and vein in the lungs of intact-chest, spontaneously breathing cats. The lobar artery catheter is of the type which allows for isolation of the left lower lobe, preferably the catheter is a triple lumen catheter with a proximal balloon. Normally, the left lower lobe is perfused with blood withdrawn from the aorta at a constant flow rate with the use of a peristaltic pump. However, blood flow can be stopped for a given period of time by stopping the pump. Also, with the use of fluoroscopy and a bronchial blocker, ventilation to the left lower lobe can be interrupted for the same period of time while blood flow is stopped. Ventilation and blood flow are interrupted for a period of time and then resumed. Lung injury following these periods of ischemia and reperfusion is characterized by the presence of leukocytes, red blood cells, macrophages and edema in the alveoli, as compared to controls. The morphological changes produced by two hours of ischemia followed by two hours of reperfusion were similar to those described by others in other species, including rats, rabbits and dogs. Zamora CA, et al, J Appl Physiol 74:224–229, 1993; Murata T, et al., *Am Rev Resp Dis* 146:1048–1053, 1992; Hamvas A, et al., *J Appl Physiol* 72:621–628, 1992.

Using this model, it has now been found that selective $A_1$ adenosine receptor antagonists administered prior to the period of ischemia markedly attenuate the alveolar injury from ischemia followed by reperfusion. The term "selective $A_1$ adenosine receptor antagonist" refers to antagonists which bind preferentially to the $A_1$ adenosine receptor and do not affect the $A_2$ adenosine receptor. Examples of antagonists selective for Am adenosine receptors include, but are not limited to, 1,3-dialkyl-8-polycycloalkyl-xanthine derivatives, preferably, 8-cyclopentyl-1,3-dipropylxanthine (DPCPX), xanthine amine cogener (XAC), xanthine carboxylic cogener (XCC), 8-(noradamantan-3-yl)-1,3-dipropylxanthine, 8-cyclopropylmethyl)-1,3-dipropyl xanthine (KW 3902), 1-propyl-3-(4-amino-3-iodophenylethyl)-8-cyclopentylxanthine (BW-A844U), and 1,3-dipropyl-8-sulfophenylxanthine (DPSPX), and 7-deaza-2-phenyladenine compounds, preferably (R)-7,8-dimethyl-2-phenyl-9-(1-phenylethyl)-7-deazaadenine. Other examples include, but are not limited to, 7,8-dihydro-8-ethyl-2-(3-noradamantyl)-4-propyl-1H-imidazo[2,1-i]purin-5(4H)-one and (±)-$N^6$-endonorbornan-2-yl-9-methyladenine (N-0861).

It has also been found that compositions comprising a selective $A_1$ adenosine receptor antagonist are effective in preventing tissue injury related to endotoxin. In the lung, endotoxin produces a transient rise in pulmonary artery pressure within 30–60 minutes, pulmonary capillary leak associated with ultrastructural changes in pulmonary capillary endothelial cells and microthrombosis by 60 minutes and a late pulmonary hypertension which lasts for several hours. The mechanisms of these pathophysiological changes in the lung following endotoxin are not completely understood. The acute, transient rise in pulmonary artery pressure following endotoxin is associated with increased lymph and blood levels of thromboxane and can be attenuated with cyclooxygenase inhibitors, thromboxane synthesis inhibitors and thromboxane receptor antagonists. Moreover, in the cat endotoxin produced acute pulmonary hypertension which was attenuated by cyclooxygenase inhibition. Pretreatment with a composition comprising the selective $A_1$ adenosine receptor antagonist, was found to significantly decrease the amount of alveoli injured following administration of endotoxin in cats.

In the present invention compositions are also provided which are useful in the prevention and/or treatment of organ injury in an animal, preferably a human, resulting from ischemia followed by reperfusion. Such compositions comprise a selective adenosine $A_1$ receptor antagonist, preferably XAC or DPCPX. It is preferred that these compositions be administered prior to ischemia, preferably 30 minutes prior to ischemia. However, compositions may be administered after ischemia but prior to reperfusion if required due to the condition causing the injury. It is preferred that these compositions be administered by intravenous bolus injection or infusion directly to the organ. Such compositions may further comprise a pharmaceutically acceptable carrier. Pharmaceutically acceptable carriers include, but are not limited to, saline, water or dextrose and water, Molecusol™ (Pharmatec Inc., Alachua, Fla.) or similar sugar solution and low dose sodium hydroxide (approximately 0.2N) solutions.

The following non-limiting examples are provided for illustrative purposes only.

EXAMPLES

Example 1

The cats are anesthetized with pentobarbital sodium, 30 mg/kg, IV, and are strapped in the supine position to a fluoroscopic table. The cats spontaneously breathe room air enriched with oxygen through a cuffed endotracheal tube. A specially designed 6F triple lumen balloon perfusion catheter is passed, under fluoroscopic guidance, from an external jugular vein into the arterial branch to the left lower lung lobe. After the lobar artery is vascularly isolated by distension of the balloon cuff on the catheter and the cat is heparinized (1000 U/kg, IV), the lobe is perfused with blood withdrawn from the femoral artery through the catheter lumen immediately beyond the balloon cuff. Perfusion pressure in the lobar artery is measured through the third lumen, 5 mm distal to the perfusion port. The lobe is perfused with a Harvard model 1210 peristaltic pump, and the perfusion rate is adjusted so that arterial pressure in the perfused lobe approximates mean pressure in the main pulmonary artery and is not changed during an experiment. Flow rates in the left lower lobe range from 35–45 ml/min. Left atrial pressure is measured with a transseptally placed 5 F Teflon catheter. Aortic pressure is measured with a 3 or 4 F catheter, inserted into the aorta by way of a femoral artery. All vascular pressures are measured with Gould transducers zeroed at right atrial level, and mean pressures, obtained by electronic integration, are recorded on a Gould recorder.

Following catheter placements, the animals are allowed to recover for one hour. During the ischemia period, the Harvard peristaltic pump is stopped and the circuit is attached to the femoral vein catheter. The femoral vein is perfused at 35 ml/min with the Harvard peristaltic pump during the period of ischemia with blood withdrawn from the aorta which normally perfuses the left lower lobe. Also, with the use of fluoroscopy a 4 F bronchial blocker is inserted into the left lower lobe bronchus and a balloon is distended with contrast dye. Ventilation to the left lower lobe is blocked during the period of ischemia. After the ischemic interval of two hours, the left lower lobe is perfused for two hours at a rate of 35 ml/min with the use of the Harvard peristaltic pump with blood withdrawn from the aorta and the bronchial blocker is removed.

Example 2

Following two hours of ischemia (when there is no blood flow or ventilation to the left lower lobe) and two hours of reperfusion, the ischemia-reperfusion injury in the cats was quantitated using light microscopy. During two hours of ischemia and two hours of reperfusion the animals were stable. Lung injury was characterized by a significant increase in percent of injured alveoli as evidenced by the presence of leukocytes, red blood cells, macrophages and edema, as compared with control animals undergoing two hours of perfusion only. These morphological changes produced by two hours of ischemia followed by two hours of reperfusion were similar to those described by others in other species, including rats, rabbits and dogs. In the control lungs, although a few cells were present there was no evidence of edema formation.

Example 3

Figure 2:
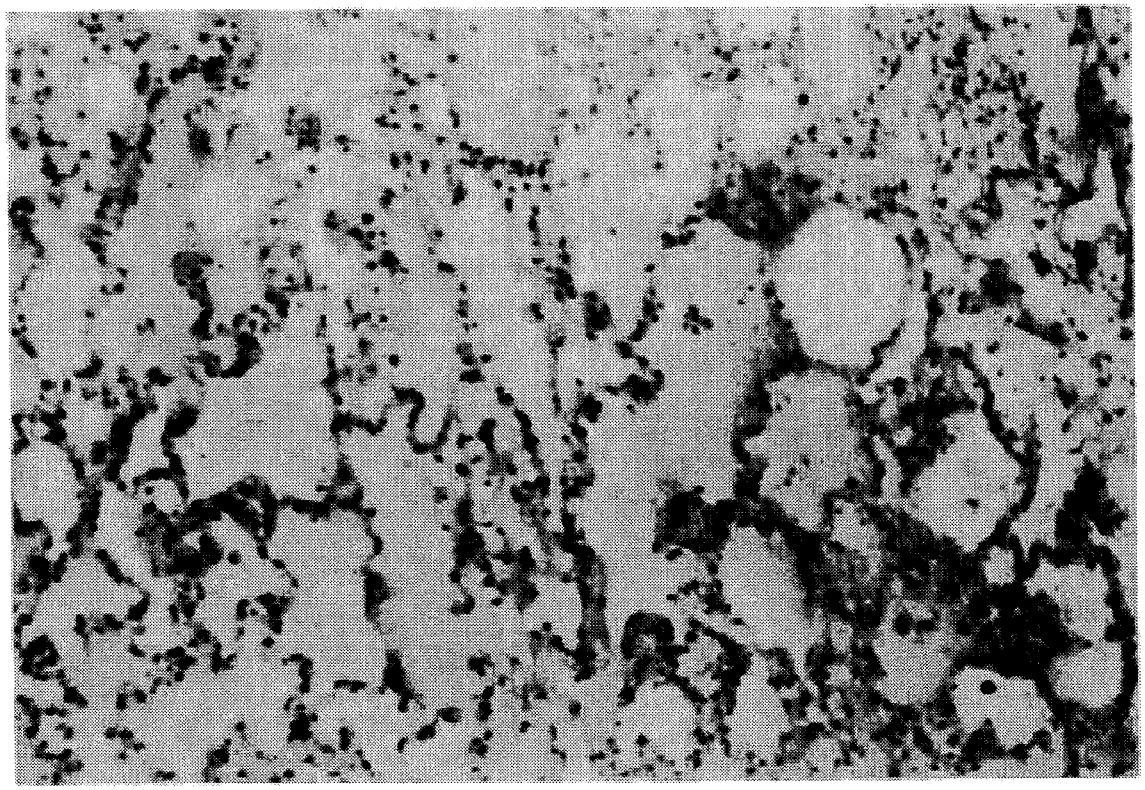
FIG. 2 is a photograph of the alveolar injury in the lung of a cat resulting from two hours of ischemia followed by reperfusion.
Figure 3:
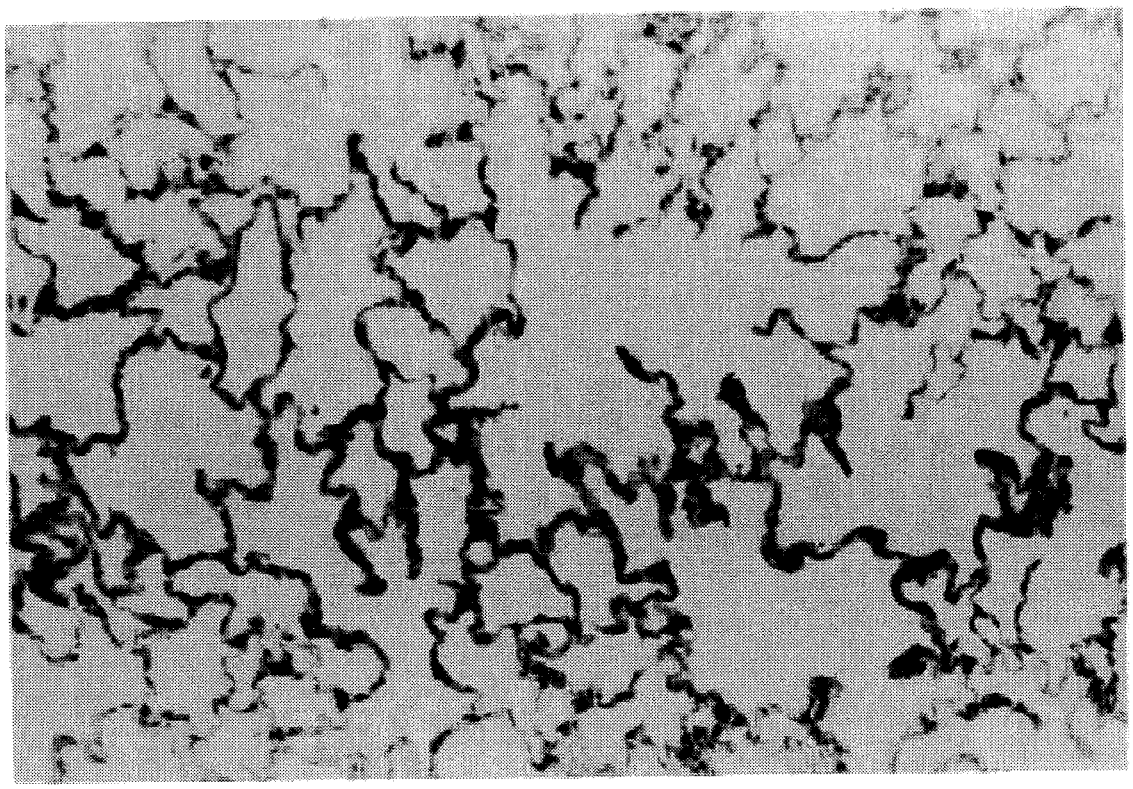
FIG. 3 is a photograph of the alveoli in the lung of a cat.

The selective $A_1$ adenosine receptor antagonist, XAC, was administered to the cats as a continuous intralobar infusion (0.075 mg/kg/hr) for 30 minutes into the left lower lobe. After 30 minutes, ventilation and blood flow to the left lower lobe were stopped for two hours. Following two hours of reperfusion, the lungs were examined as described in Example 2 for alveolar injury. In animals pretreated with XAC only 8% of the alveoli were injured after ischemia-reperfusion (see FIG. 1. In animals not receiving the treatment 59% of the alveoli were injured after ischemia-reperfusion (see FIG. 2). Thus, pretreatment with the selective $A_1$ adenosine receptor antagonist markedly attenuated the alveolar injury following two hours of ischemia and two hours of reperfusion. Morphologically, the percentage of injured alveoli after XAC prior to ischemia-reperfusion was not significantly different from controls (8% XAC vs. 4.8% controls (see FIG. 3)).

Example 4

The selective $A_1$ adenosine receptor antagonist, DPCPX, was administered to the cats (6 mg/kg, i.v.). After 30 minutes, ventilation and blood flow to the left lower lobe were stopped for two hours. Following two hours of reperfusion, the lungs were examined as described in Example 2 for alveolar injury. In animals pretreated with DPCPX only 13.4% of the alveoli were injured after ischemia-reperfusion. In animals not receiving the treatment 59% of the alveoli were injured after ischemia-reperfusion. Thus, pretreatment with the selective $A_1$ adenosine receptor antagonist markedly attenuated the alveolar injury following two hours of ischemia and two hours of reperfusion. Morphologically, the percentage of injured alveoli after DPCPX prior to ischemia-reperfusion was not significantly different from controls (13.4% DPCPX vs. 4.8% controls).

Example 5

The selective $A_1$ adenosine receptor antagonist, DPCPX, was administered to cats (5 mg/kg, i.v.). After thirty minutes endotoxin (15 mg/kg) was administered to these cats as a continuous intralobar infusion over 30 to 40 minutes into the left lower lobe. Following a two hour period the lungs were examined as described in Example 2 for alveolar injury. In animals pretreated with DPCPX only 9.2% of the alveoli were injured following administration of the endotoxin. In animals not receiving the DPCPX 83% of the alveoli were injured following administration of endotoxin. Thus, pretreatment with the selective $A_1$ adenosine receptor antagonist, DPCPX, markedly attenuated the alveolar injury following administration of endotoxin. Morphologically, the percentage of injured alveoli after DPCPX pretreatment was not significantly different from controls (9.2% DPCPX rs. 4.8% controls).

What is claimed is:

1. A method of preventing ischemia-reperfusion organ injury comprising administering to an animal an effective amount of a selective $A_1$ adenosine receptor antagonist at a selected time prior to a surgical procedure in which ischemia is expected to occur so that organ injury resulting from the surgical procedure is prevented.

2. The method of claim 1 wherein the animal is a human.

3. The method of claim 1 wherein the organ injury is in lung tissue.

4. The method of claim 1 wherein the surgical procedure comprises organ transplantation.

5. A method of inhibiting organ injury in high risk patients for ischemia-reperfusion injury comprising administering to a patient an effective amount of a selective $A_1$ adenosine receptor antagonist so that injury from ischemiareperfusion is inhibited.

6. The method of claim 5 wherein the ischemiareperfusion injury is resulting from a bowel ischemia and reperfusion, sepsis, anaphylaxis, hemorrhagic shock, or trauma.

7. The method of claim 1 wherein the selective $A_1$ adenosine receptor antagonist of the composition comprises an alkyl xanthine derivative.

8. The method of claim 1 wherein the selective $A_1$ adenosine receptor antagonist of the composition comprises a 7-deaza-2-phenyladenine compound.

9. The method of claim 1 wherein the selective Am adenosine receptor antagonist of the compositions is DPCPX, XAC, XCC, 8-(noradamantan-3-yl)-1,3-dipropylxanthine, 8-cyclopropyl-methyl)-1,3-dipropyl xanthine, 1-propyl-3-(4-amino-3-iodophenylethyl)-8-cyclopentylxanthine, DPSPX, 7,8-dihydro-8-ethyl-2-(3-noradamantyl)-4-propyl-1H-imidazo[2,1-i]purin-5(4H)-one, (R)-7,8-dimethyl-2-phenyl-9-(1-phenylethyl)-7-deazaadenine or (±)-$N^6$-endonorbornan-2-yl-9-methyladenine.

10. The method of claim 1 wherein the selective $A_1$ adenosine receptor antagonist is XAC.

11. The method of claim 1 wherein the selective $A_1$ adenosine receptor antagonist is DPCPX.

* * * * *